United States Patent [19]

Vishwakarma

[11] Patent Number: 5,670,654
[45] Date of Patent: Sep. 23, 1997

[54] METHOD OF SYNTHESIZING 2-(2'-HYDROXYPHENYL) BENZOTRIAZOLE COMPOUNDS

[75] Inventor: Lal Chand Vishwakarma, Rochester, N.Y.

[73] Assignee: Eastman Kodak Company, Rochester, N.Y.

[21] Appl. No.: 602,946

[22] Filed: Feb. 16, 1996

Related U.S. Application Data

[60] Provisional application No. 60/000,663, Jun. 29, 1995.
[51] Int. Cl.$^6$ ................................................. C07D 249/20
[52] U.S. Cl. ............................................ 548/260; 548/259
[58] Field of Search ...................................... 548/259, 260

[56] References Cited

U.S. PATENT DOCUMENTS

| | | | |
|---|---|---|---|
| 3,072,585 | 1/1963 | Milionis et al. | 260/22 |
| 3,214,436 | 10/1965 | Boyle et al. | 260/308 |
| 4,745,194 | 5/1988 | Vogl et al. | 548/260 |
| 4,921,966 | 5/1990 | Stegmann et al. | 548/260 |
| 4,999,433 | 3/1991 | Prestel et al. | 548/260 |
| 5,276,161 | 1/1994 | Prestel et al. | 548/260 |
| 5,372,922 | 12/1994 | Schofield et al. | 430/572 |

FOREIGN PATENT DOCUMENTS

| | | |
|---|---|---|
| 0 190 003 | 8/1986 | European Pat. Off. . |
| 1324897 | 3/1963 | France . |
| 1324898 | 3/1963 | France . |
| 63/55542 | 3/1988 | Japan . |
| 991204 | 5/1965 | United Kingdom . |
| 991320 | 5/1965 | United Kingdom . |
| 991142 | 5/1965 | United Kingdom . |
| 991630 | 5/1965 | United Kingdom . |

OTHER PUBLICATIONS

Freeman et al., "An Approach to the Design of Lightfast Disperse Dyes—Analgos of Disperse Yellow 42", 12 May 1992, pp. 172–195.

Judi Rosevear & John F. K. Wilshire, "The Reduction of Some o-Nitrophenylazo Dyes With Thiourea S,S-Dioxide (Formamidinesulfinic Acid): A General Synthesis of 2-Aryl-2H-Benzotriazoles and Their 1-Oxides", pp. 2489–2497 (1984).

Judi Rosevear & John F. K. Wilshire, "Preparation of Some 2-(Methoxyphenyl)-2H-Benzotriazoles and the Corresponding Hydroxyphenyl Compounds", pp. 1663–1673 1987.

*Primary Examiner*—Patricia L. Morris
*Attorney, Agent, or Firm*—Edith A. Rice

[57] ABSTRACT

A method for preparing a compound of formula (VII):

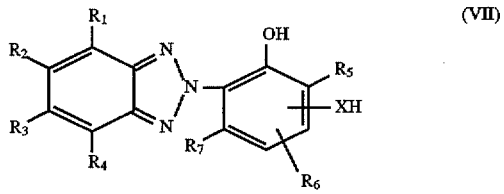

(VII)

wherein:

$R_1$, $R_2$, $R_3$, $R_4$, $R_5$, $R_6$, $R_7$ and X are defined in the specification;

the method comprising:

protecting at least —XH on a compound of formula (IV) below to form a protected formula (IV) compound, by forming —X(PG) where PG is a group other than H which is not removed during a subsequent ring closure step:

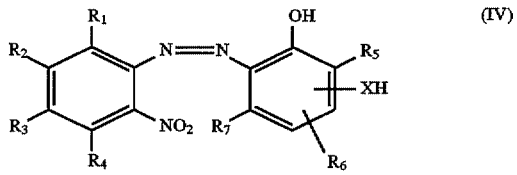

(IV)

performing a ring closure by reacting the protected formula (IV) compound with a reducing agent to form a compound of formula (VI):

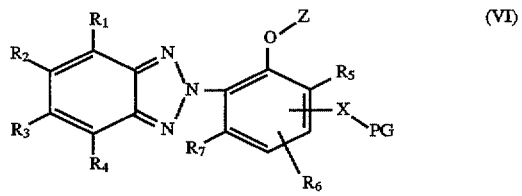

(VI)

wherein Z is H or a protecting group;

deprotecting the compound of formula (VI) to form the compound of formula (VII) by replacing PG with H and, when Z is not H, also replacing Z with H.

28 Claims, No Drawings

METHOD OF SYNTHESIZING 2-(2'-HYDROXYPHENYL) BENZOTRIAZOLE COMPOUNDS

CROSS REFERENCE TO RELATED APPLICATION

Reference is made to and priority claimed from U.S. Provisional application Ser. No. U.S. 60/000,663 filed 29 Jun. 1995, entitled METHOD OF SYNTHESIZING 2-(2'-HYDROXYPHENYL)BENZOTRIAZOLE COMPOUNDS.

FIELD OF THE INVENTION

This invention relates to a method of synthesizing 2-(2'-hydroxyphenyl)benzotriazole compounds which are useful as precursors in the synthesis of ultraviolet absorbing compounds.

BACKGROUND OF THE INVENTION 2-(2'-Hydroxyphenyl)benzotriazole compounds are known in the art as ultraviolet absorbing compounds useful for paints, plastics, polymers, and coatings. Such compounds are particularly used in silver halide photographic elements particularly useful for protection of yellow, magenta and cyan image dyes from fading in color photographic prints. Such compounds with a 4'- or 5'-hydroxy or amino substituent are known in the prior art, and are used to prepare various ultraviolet absorbing derivatives of the 4'- or 5'-substituent. For example, the use of such 4'- or 5'-hydroxy or amino substituted compounds are described in U.S. Pat. No. 3,123,058; U.S. Pat. No. 3,072,585; EP 0 190 003; U.S. Pat. No. 5,372,922 and Japanese published patent application (Kokai) No. 63[1988]-55542; FR 1,330,378; FR 1,324,898; FR 1,324,897; GB 991 204; GB 991 320; GB 991 142; GB 991 630, and GB 991 204 and the references described in them.

Commercially available 2-(2'-hydroxyphenyl) benzotriazoles of formula (VIII) below:

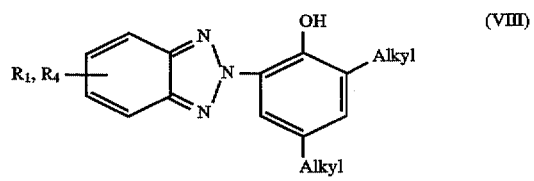

(VIII)

containing 3',5'-dialkyl substituents (or just one or no alkyl substituent), appear to be readily obtainable from their corresponding azo dyes by known reductive ring closure methods. On the other hand, similar compounds to those of formula (VIII) but also having a 4'- or 5'-amino or hydroxy substituent (see formula (VII) below), are difficult to obtain in high yields by reductive ring closure of the corresponding azo dye compounds of formula (IV):

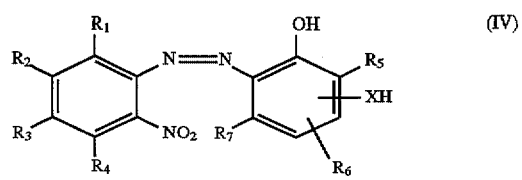

(IV)

where X is O, S or NR$_8$.

In an article by J. Rosevear and J. F. K. Wilshire in *Australian Journal of Chemistry*, Vol. 40, Page 1663–1673 (1987) there is described a method of making 2-(2',4'-dihydroxyphenyl)benzotriazoles in which the corresponding azo dyes with 2',4'-dimethoxy substituents are first made. These are then ring closed with thiourea-S,S-dioxide. The 2',4'-dimethoxy substituted dyes are formed by reaction of the corresponding methoxy substituted anilines with 2-nitronitrosobenzenes. A difficulty with the foregoing procedure, however, is that the 2',4'-dimethoxy substituted azo dyes are obtained in relatively low yields (0% to 67%). Furthemore, the corresponding dimethoxy aniline must be used as a starting reagent. U.S. Pat. No. 3,072,585 describes ring closure of a 2',4'-dihydroxy substituted azo dye using zinc dust, to obtain the corresponding benzotriazole compound. However, the yields obtained are relatively low. Furthermore, zinc dust is environmentally unacceptable for many situations.

It would be desirable then, to provide an alternative process for preparing 2-(2'-hydroxyphenyl) benzotriazole compounds having a 4'- or 5'-hydroxy or amino substituent, which process can provide good overall yields, and which is enviromentally sound.

SUMMARY OF THE INVENTION

The present invention realizes that in preparing a compound of formula (VII) below, the intermediate corresponding azo dye is beneficially first prepared with unprotected hydroxy or aminophenols (that is, —OH, —NH$_2$ or —NHR$_8$). Such groups can then be protected before reductive ring closure to form the corresponding benzotriazole compound, the protective groups being removed to form compound (VII).

Accordingly, the present invention provides a method for preparing a compound of formula (VII):

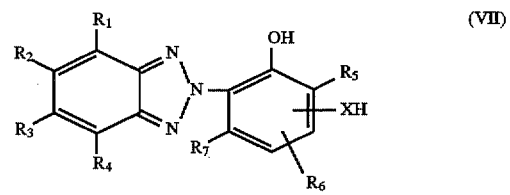

(VII)

wherein:

R$_1$, R$_2$, R$_3$, R$_4$, R$_5$, R$_6$ and R$_7$ are, indepedently: H; halogen; cyano; —CO$_2$Y where Y is H or a 1 to 12 (preferably 1 to 6) carbon atom alkyl or 6 to 20 (preferably 6 to 10) carbon atom aryl group; 1 to 12 (preferably 2 to 9) carbon atom carbamoyl group; 0 to 12 (preferably 2 to 4) carbon atom sulfoxido group; 0 to 12 (preferably 1 to 10) carbon atom sulfonyl group; 0 to 12 (preferably 1 to 10) carbon atom sulfonato group; 0 to 12 (preferably 1 to 10) carbon atom sulfonamido group; 1 to 18 (preferably 1 to 10) carbon atom alkyl group; 1 to 18 (preferably 1 to 10) carbon atom alkoxy group; 6 to 20 (preferably 6 to 10) carbon atom aryl group; 5 to 20 (preferably 5 to 10) atom heteroaryl group having 1 to 4 (preferably 1 to 3) heteroatoms selected from O, N or S; 6 to 20 (preferably 6 to 10) carbon atom aryloxy group; or any two or more of adjacent ones of R$_1$ through R$_4$, or R$_6$ and R$_7$ together, or R$_6$ and R$_5$ together when they are adjacent one another, may together form a 1 to 10 carbon atom alicyclic group, or complete, together with the carbon atoms of the benzene ring to which they are attached, a 6 to 20 (preferably 6 to 10) carbon atom aromatic group or a 5 to 20 (preferably 5 to 10) atom heteroaryl group having 1 to 4 (preferably 1 to 3) heteroatoms selected from O, N or S; or R$_7$ is OH;

X is O, D, or NR$_8$ where R$_8$ is H, 1 to 12 (preferably 1 to 6) carbon atom alkyl or 6 to 20 (preferably 6 to 10) carbon atom aryl group, or 5 to 20 (preferably 5 to 10) atom heteroaryl group having 1 to 4 (preferably 1 to 3) heteroatoms selected from O, N or S;

the method comprising:

protecting at least —XH on a compound of formula (IV) below to form a protected formula (IV) compound, by forming —X(PG) where PG is a group other than H which is not removed during a subsequent ring closure step:

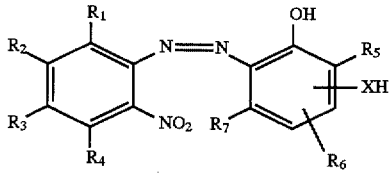

wherein $R_1$ to $R_7$ and X are as defined above for formula (VII);

performing a ring closure by reacting the protected formula (IV) compound with a reducing agent to form a compound of formula (VI):

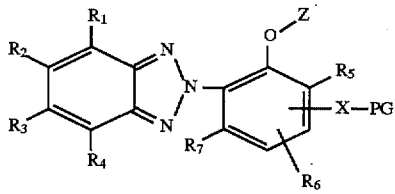

wherein Z is H or a protecting group;

deprotecting the compound of formula (VI) to form the compound of formula (VII) by replacing PG with H and, when Z is not H, also replacing Z with H.

EMBODIMENTS OF THE INVENTION o-Nitroazobenzenes of type (IV-A) and (IV-B) may easily exist in keto form (IX) and in imino form (X):

benzotriazoles by preventing formation of the keto and imino forms of (IV-A) and (IV-B). Reductive ring closure of protected azo dyes may then easily be accomplished by commonly used reducing agents known in the art, for example, thiourea-S,S-dioxide, saccharides containing an aldehyde group in presence of fluorenol as a catalyst, ammonium salts of formic acid in presence of Pd-C, and the like. Thus, the use of traditionally used zinc dust, which may be environmentally unacceptable, can be eliminated. Deprotection after the ring closure may be accomplished by conventional methods known in the art.

In the above formula (I), when reference is made to adjacent ones of $R_1$ through $R_7$, this means that they are attached to carbon atoms on the benzene or 2'-hydroxyphenyl rings shown, which carbon atoms are bonded to one another. It is also preferred that $R_3$ is F, Cl, Br, cyano, carboxy, carbalkoxy, 1 to 18 (preferably 1 to 8) carbon atom alkoxy group, or 0 to 12 (preferably 1 to 10) carbon atom sulfonyl group; $R_7$ is H or OH; $R_5$ and $R_6$ are independently a 1 to 12 (preferably 1 to 8) carbon atom alkyl or H; and $R_1$ and $R_2$ are independently H, Cl or a 1 to 18 (preferably 1 to 8) carbon atom alkoxy group.

In the method of the present invention, —OH is also protected on formula (IV) prior to the ring closure step, to form —O(PG$_1$), wherein PG$_1$ is a group other than H which is not removed during a subsequent ring closure step or is a 1–12 (or 2 to 12, but preferably 1 to 10) carbon atom acyl group, 1 to 24 (preferably 2 to 10) carbon atom carbamyl group, or a 1 to 12 (preferably 1 to 10) carbon atom sulfonyl group. PG$_1$ therefore may be the same or different from PG.

In reference to PG or PG$_1$ not being removed during the subsequent ring closure step, is meant that more than 50% (preferably more than 70%, most preferably more than 90%) remains on the compound of formula (VI) after the ring closure step before deprotection. Various groups which are suitable for PG and PG$_1$ include: 1–18 (preferably 1 to 10) carbon atom alkyl group with or without 1 to 6 intervening oxygen, sulfur or nitrogen atoms; 1–18 (preferably 1 to 10) carbon atom acyl group; 1 to 24 (preferably 2 to 10) carbon

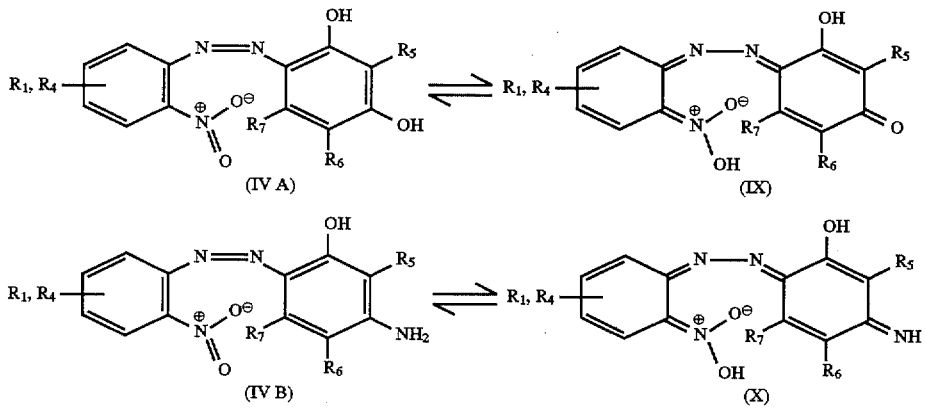

due to extended conjugation. This may complicate the reductive ring closure giving several unexpected side products as a result of breakage of N—N single bond or just complete reduction of the nitro to amino group, and other problems. These factors may significantly reduce yield of the desired products (VII).

While not being limited by the present description, it is believed that the protection of OH and NH$_2$ groups as described above (such that there are no free H on them), assists in providing a clean and effective ring closure to atom carbamyl group; 1 to 18 (preferably 1 to 10) carbon atom sulfonyl group; benzyl group; tetrahydropyranyl group; and 3 to 20 (3 to 10) carbon atom trialkyl silyl group. Examples of such groups include methyl; ethyl; n-propyl; isopropyl; butyl; pentyl; t-butyl; t-amyl; methoxymethyl; methoxyethoxymethyl; formyl; acetyl; benzoyl; SO2R$_{10}$ where R$_{10}$ is selected from methyl, ethyl, phenyl or p-toluenesulfonyl; 1 to 12 carbon atom dialkyl carbamyl (for example, dimethylcarbamyl, or diethylcarbamyl); benzyl group; tetrahydropyranyl group; and 3 to 20 carbon atom trialkyl silyl group (such as trimethylsilyl); or COR$_9$ where R$_9$ is methyl, ethyl or phenyl; phenyl group; pyridinyl; imidazoyl; pyrrolyl; furyl; and thienyl.

When R$_7$ in (VII) is OH, that OH is also protected on formula (IV) prior to the ring closure step, to form —O(PG$_1$), wherein PG$_1$ is a group other than H which is not removed during a subsequent ring closure step, or is a 1–12 carbon atom acyl group, 1 to 24 carbon atom carbamyl group, or a 1 to 12 carbon atom sulfonyl group. Examples of suitable PG$_1$ are the same as those given for PG$_1$ described above.

The method of the present invention may also encompass the formation of the compound of formula (IV) by diazotizing the compound of formula (I) with an aqueous acidic nitrite salt to obtain the compound of formula (II), and coupling the compound of formula (II) with the compound of formula (III) to obtain the compound of formula (IV), as shown below in Scheme 1.

Scheme 1

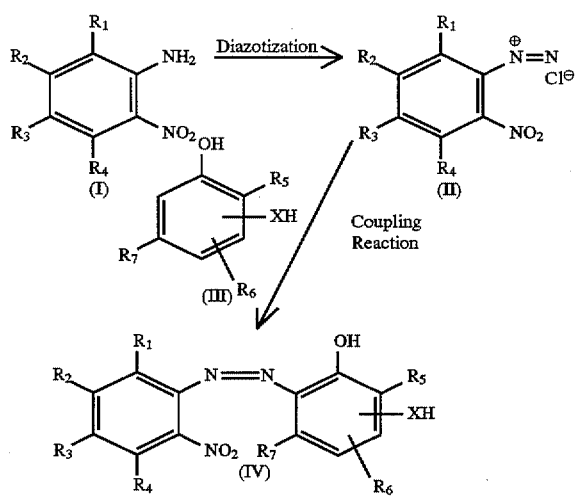

wherein R$_1$ to R$_7$ and X are as defined above for formula (VII).

The present invention can use the diazotization step to prepare unprotected compounds of formula (IV) in yields from 87 to 99% by diazotizing 2-nitroanilines and condensing with corresponding resorcinol, phloroglucinol or 3-aminophenols, or 4-aminophenols following the general procedure known in the art, for example: U.S. Pat. Nos. 3,072,585; 3,159,646; 3,813,255; and 4,780,541; pending U.S. patent application Ser. No. 08/313,492; and FR 1,330, 378; FR 1,324,898; FR 1,324,897; GB 991 204; GB 991 320; GB GB 991 630; and GB 991 204 and the references described in them. Those references and all other references cited in the present application, are incorporated herein in their entirety by reference.

As to the protection of compounds of formula (IV), as already described various protection groups can be used. It will be appreciated that the exact reaction conditions which may be used will depend on the protecting group being used. Reaction conditions for various protecting groups are described in more detail in the references cited below.

As to the ring closure step, this is preferably accomplished by reacting the protected formula (IV) compound with a reducing agent selected from a thiourea-S,S-dioxide and a dithionite salt (such as an alkali metal salt, for example, sodium or potassium dithionite) in a basic aqueous solution. The aqueous solution is preferably an alcoholic aqueous solution, and the reaction temperature may be maintained at about 60° to 80° C. for about 2 to 3 hours. The alcohols may be selected, for example, from ethanol, methanol, and isopropanol. The solution may, for example, be between 1 to 6N hydroxide ion. A preferred solution is 4N sodium hydroxide in a 50/50 (by volume) methanol/water solution.

As to the ring closure step, this can be accomplished by various known methods. These include catalytic hydrogenation of the protected formula (IV) compound. Catalytic hydrogenation is usually accomplished with high pressure (for example, 2–20 atmospheres) hydrogen gas in the presence of a catalyst such as palladium-charcoal or platinum, or a combination of platinum and palladium. Another ring closure step uses a suitable hydrogen donor, such as formate salt (for example, an alkali metal salt such as sodium or potassium formate, or ammonium formate) in the presence of a catalyst (such as a palladium-charcoal catalyst). Ring closure can also be accomplished using the conventional zinc reduction method such as described in U.S. Pat. No. 3,072,585. Use of the zinc dust method still gives better results than when an unprotected azo dye compound is used. However, the use of zinc is considered less desirable due to potential adverse environmental impact from zinc use.

As to the deprotection step, as will be appreciated the exact conditions to be used will vary depending upon the particular protecting group used. In the case of certain groups which are used to protect the 2'-hydroxy or R$_7$ when R$_7$ is hydroxy (these groups being referenced herein as PG$_1$), in some cases these may deprotect during ring closure. Such groups include a 1–12 carbon atom acyl group, 1 to 24 carbon atom carbamyl group, or a 1 to 12 carbon atom sulfonyl group. These specific groups are removed by hydrolysis during the ring closure step (other than during catalytic hydrogenation). Specifically, the foregoing specific groups are removed during ring closure using thiourea-S,S-dioxide or a dithionite salt.

When PG or PG$_1$ is selected from a 1 to 18 carbon atom alkyl group or a benzyl group, the protected compound of formula (VI) may be deprotected in the presence of a boron trihalide in a halogenated hydrocarbon solvent. Examples of suitalbe halogenated hydrocarbon solvents include methylene chloride, chloroform, and dichloroethane. Additionally, when either is a benzyl group they can be deprotected by aqueous mineral acid or by catalytic hydrogenation with palladium-charcoal catalyst. When PG is selected from 1–18 carbon atom acyl group, 1 to 24 carbon atom carbamyl group, or 1 to 18 carbon atom sulfonyl group, the compound of formula (VI) may, for example, be deprotected by aqueous acidic or basic hydrolysis.

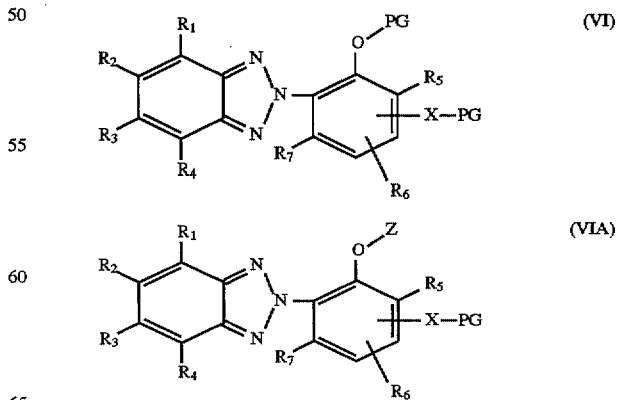

When PG is selected from a benzyl group or a tetrahydropyranyl group, the compound of formula (VI) may be deprotected by reacting with an aqueous mineral acid. When PG is selected from a 3 to 20 carbon atom trialkyl silyl group, then the compound of formula (VI) is deprotected by reacting with an aqueous fluoride salt (such an alkali metal fluoride, such as potassium or sodium fluoride, or tetrabutyl ammonium fluoride) in the presence of an organic co-solvent (preferably as tetrahydrofuran). Examples of mineral acids include sulfuric, phosphoric and hydrochloric acids.

It is preferred that all of the steps of the synthesis of the present invention, are performed without isolating products (other than the final product of compound (VII). By "not isolating" in this context is meant that solvents or other volatile compounds may be removed, but non-volatile compounds are not removed and intermediates are not isolated.

The nitroanilines which may be used for diazotization include, but are not limited to, 2-nitroaniline, 6-methoxy-2-nitroaniline, 4-methoxy-2-nitroaniline, 4,5-dimethoxy-2-nitroaniline, 4-chloro-2-nitroaniline, 4-fluoro-2-nitroaniline, 4-bromo-2-nitroaniline, 4,5-dichloro-2-nitroaniline, 4-cyano-2-nitroaniline, 4-carboxy-2-nitroaniline and the like.

The phenols which can be used as coupling components include, but are not limited to, 3-aminophenol, resorcinol, phloroglucinol, 4-chlororesorcinol, 4-fluororesorcinol, 4-cyanoresorcinol, 4-carboxy resorcinol, 4-ethyl resorcinol, 4-methyl resorcinol, 4-propylresorcinol and the like.

Examples of 2-nitroazobenzenes of formula (IV) include, but are not limited to:

2-nitro-(2',4'-dihydroxyphenyl)azobenzene,
2-nitro-(2'-hydroxy, 4'-aminophenyl)azobenzene,
2-nitro-(2',4',6'-trihydroxyphenyl)azobenzene,
2-nitro-4-chloro-(2',4'-dihydroxyphenyl)azobenzene,
2-nitro-4-fluoro-(2',4'-dihydroxyphenyl)azobenzene,
2-nitro-4-methoxy-(2',4'-dihydroxyphenyl)azobenzene,
2-nitro-4,5-dimethoxy-(2',4'-dihydroxyphenyl)azobenzene,
2-nitro-4-methyl-(2',4'-dihydroxyphenyl)azobenzene,
2-nitro-(2',4'-dihydroxy-5'-chlorophenyl)azobenzene,
2-nitro-(2',4'-dihydroxy-5'-fluorophenyl)azobenzene,
2-nitro-(2',4'-dihydroxy-5'-ethylphenyl)azobenzene,
2-nitro-4,6-dichloro-(2',4'-dihydroxyphenyl)azobenzene, An important aspect of the present invention is "direct protection" of azo dyes of formula (IV) to give the protected azo dyes of formula (V) shown below.

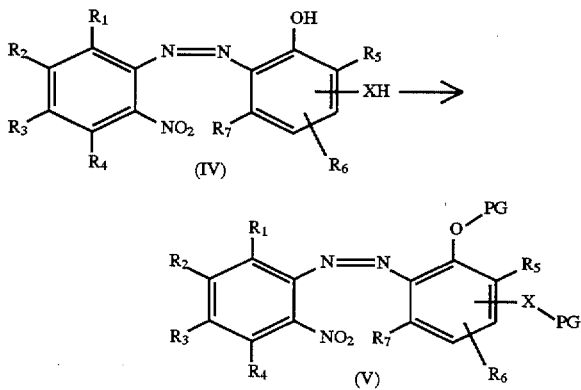

(IV)

(V)

The following protecting groups, such as methyl(Me); iso-propyl(i-Pr); benzyl(Bz); trimethylsilyl(TMS); tetrahydropyranyl (THP); acetyl(Ac); p-toluenesulfonyl(PTS); dialkyl carbamyl such as dimethyl carbamyl; methoxymethyl(MOM); methoxyethoxymethyl(MEM); t-butoxymethyl and benzoyl groups etc. may be used.

Protection and deprotection of phenolic and amino groups are well known in the art. The book on this subject by T. W. Greene, "Protective Groups in Organic Synthesis", 2d ed., Wiley interscience, New York, 1991, may be referred to for necessary details. Other important references usable in the present invention include, for example, sulfonylation and desulfonylation of phloroglucinol is described by R. S.-Obregon, G. Hurtado, H. Barrios, B. Ortiz and F. Yuste in *Organic Preparations and Procedures International*, Vol. 18(3), page 145–148 (1986); an effective demethylation of phenolic ethers with silicon tetrachloride/sodium iodide has been described by M. V. Bhatt and S. S. El-Morey in *Synthesis*, page 1048 (1982) and also by C. C. Kanakam et al in *Journal of Chemical Society, Perkin Transaction I*, page 1907–1913 (1989); such demethylation also has been described by I. Rani in *Indian Journal of Chemistry*, Vol. 25B, page 1251 (1986) using anhydrous AlCl₃ in acetonitrile; use of boron tribromide in methylene chloride for demethylation is described by J. Rosevear and J. F. K. Wilshire in *Australian Journal of Chemistry*, Vol. 40, page 1663–1673(1987) (which is also cited as one of the closest prior arts of the present invention); a lot cheaper alternative for nearly quantitative demethylation has been described by F. Xi, W Basset, Jr. and O. Vogl in *Makromolecular Chemistry*, Vol. 185, page 2497–2509 (1984) by using dry hydrogen bromide gas in dry dimethylformamide; use of constant boiling hydrobromic acid (48%) for demethylation has been described by N. A. Evans in *Australian Journal of Chemistry*, Vol. 34, page 691–695 (1981); protection by tetrahydropyranyl(THP) group has been described by C. C. Kanakam et al in *Journal of Chemical Society, Perkin Transaction I*, page 1907–1913 (1989), and by R. D. Johnston et al in *Synthesis—Stuttgart*, Issue 5, page 393–394 (1988) making use of Reillex 425 hydrochloride as a catalyst. Other protecting groups listed in Table 1 are rather easily removable after the ring closure step by acid or base hydrolysis as commonly known in the art.

Table 1 illustrates examples, which are not limited in scope of this invention, of protected azo dyes of formula (VA).

TABLE 1

Protected Azo Dyes (VA)

| S. No | R₁ | R₂ | R₃ | R₄ | R₅ | R₆ | R₇ | X | PG |
|---|---|---|---|---|---|---|---|---|---|
| 1 | H | H | H | H | H | H | H | O | Me, i-Pr, Bz, TMS, THP, PTS, Carbamyl |
| 2 | H | H | Methyl | H | H | H | H | O | Me, i-Pr, Bz, TMS, THP |
| 3 | H | H | H | H | H | H | H | O | Ac, Benzoyl, PTS |
| 4 | H | H | Cl or F | H | H | H | H | O | Me, i-Pr, Bz, TMS, THP, PTS, Carbamyl |
| 5 | H | Methoxy | H | H | H | H | H | O | Ac, Benzoyl, PTS |
| 6 | H | Methoxy | Methoxy | H | H | H | H | O | Ac, Benzoyl, |

TABLE 1-continued

Protected Azo Dyes (VA)

| S. No | $R_1$ | $R_2$ | $R_3$ | $R_4$ | $R_5$ | $R_6$ | $R_7$ | X | PG |
|---|---|---|---|---|---|---|---|---|---|
| 7 | H | H | H | H | H | Et | H | O | Me, i-Pr, Bz, TMS, THP, Ac, PTS |
| 8 | H | H | H | H | H | Cl | H | O | Me, i-Pr, Bz, TMS, THP, Ac |
| 9 | H | H | H | H | H | H | H | NH | Ac, Benzoyl, PTS, TMS, THP, PTS, Carbamyl |
| 10 | H | H | F | H | H | H | H | NH | Ac, Benzoyl, PTS, TMS, THP, PTS, Carbamyl |
| 11 | H | H | H | H | H | H | Me | NEt | Ac, Benzoyl, PTS, TMS, THP, PTS, Carbamyl |
| 12 | H | H | Cl | H | H | H | Me | NEt | Ac, Benzoyl, PTS, TMS, THP, PTS, Carbamyl |
| 13 | H | H | MeO | H | H | H | Me | NEt | Ac, Benzoyl, PTS, TMS, THP, PTS, Carbamyl |

Table 2 illustrates examples, which are not limited in scope of this invention, of protected azo dyes of formula (VB).

TABLE 2

Protected Azo Dyes (VB)

| S. No | $R_1$ | $R_2$ | $R_3$ | $R_4$ | $R_5$ | $R_6$ | $R_7$ | X | PG |
|---|---|---|---|---|---|---|---|---|---|
| 1 | H | H | H | H | H | H | H | O | Me, i-Pr, Bz, TMS, THP, PTS, Carbamyl |
| 2 | H | H | Methyl | H | H | H | H | O | Me, i-Pr, Bz, TMS, THP |
| 3 | H | H | H | H | H | H | H | O | Ac, Benzoyl, PTS |
| 4 | H | H | Cl or F | H | H | H | H | O | Me, i-Pr, Bz, TMS, THP, PTS, Carbamyl |
| 5 | H | Methoxy | H | H | H | H | H | O | Ac, Benzoyl, PTS |
| 6 | H | Methoxy | Methoxy | H | H | H | H | O | Ac, Benzoyl, PTS |
| 7 | H | H | H | H | H | t-Bu | H | O | Me, i-Pr, Bz, TMS, THP, Ac |
| 8 | H | H | H | H | H | Cl | H | O | Me, i-Pr, Bz, TMS, THP, Ac |
| 9 | H | H | H | H | H | H | H | NH | Ac, Benzoyl, PTS, TMS, THP, PTS, Carbamyl |
| 10 | H | H | F | H | H | H | H | NMe | PTS or Benzoyl or carbamyl, Ac |
| 11 | H | H | Cl | H | H | H | H | NMe | PTS or Benzoyl or carbamyl, Ac |
| 12 | H | H | MeO | H | H | H | H | NMe | PTS or Benzoyl or carbamyl, Ac |
| 13 | H | MeO | MeO | H | H | H | H | NMe | PTS or Benzoyl or carbamyl, Ac |
| 14 | H | Cl | Cl | H | H | H | H | NMe | PTS or Benzoyl or carbamyl, Ac |

The reductive ring closure step can be accomplished by Scheme 2 below:

Scheme 2

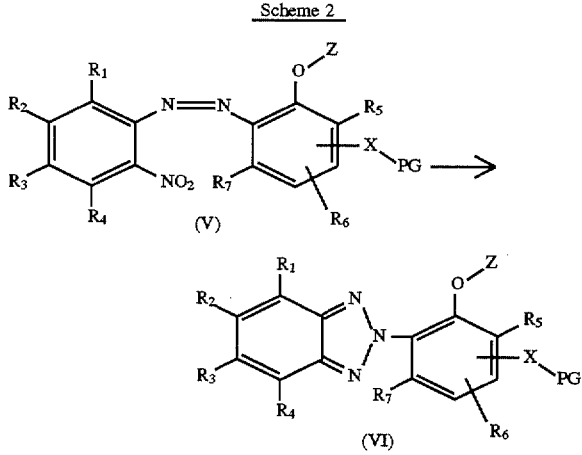

in excellent yield by use of thiourea-S,S-dioxide only if the protective group (PG) is stable to base such as sodium hydroxide under the described reaction conditions. The reductive ring closure of (V) bearing base-stable protective groups may also be accomplished by other reducing agents, such as use of sodium dithionite has been described by J. K. Makrandi and V. Kumari in *Synthetic Communications*, Vol. 20 (12), page 1885–1888 (1990); JP 92078633-B using this reagent in conjunction with sodium formate; noble metal-catalyzed hydrogenative ring closure as widely practiced in the known art; aldehyde containing saccharides as described in U.S. Pat. No. 5,262,541; and the like. The reductive ring closure of (V) bearing acid-base labile protective groups such as acetyl, benzoyl, sulfonyl and the like may be accomplished under nearly neutral conditions such noble-metal catalyzed ring closure well known in the art or by hydrogen-donating reagent such as ammonium salts of formic acid in conjunction with Pd-C.

The following non-limiting examples serve to illustrate the present invention.

EXAMPLE 1

(Direct Protection)

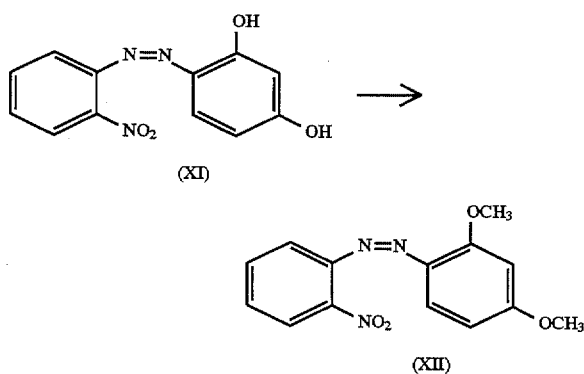

The unprotected azo dye (XI) was prepared in 99% yield by condensing 2-nitrophenyldiazonium chloride (obtained by diazotization of 2-nitroaniline with sodium nitrite in hydrochloric acid) with resorcinol following conventional procedure as known in the art previously cited. The azo dye (XI) was used in this reaction without further crystallization as it was 98–99% pure by HPLC assay. A mixture of unprotected azo dye (XI) (25.9 g, 0.10 mole), dimethyl sulfate (31.53 g, 0.25 mole, 23.66 mL), anhydrous potassium carbonate(69.0 g, 0.5 mole), and dry acetone (600 mL) was refluxed in a 2-L 3-necked round bottom flask equipped with a mechanical stirrer, water condenser and argon gas-inlet. The reaction mixture was refluxed for 16 hours with vigorous mechanical stirring. The reaction was monitored by TLC using silica gel plates and methylene chloride as the developing solvent. Also HPLC showed just one peak corresponding to product (XII) having retention time 16.3 min. The reaction mixture was cooled to room temperature and filtered through a sintered glass funnel of medium porosity to remove inorganic solid which was well washed with acetone (4×50 mL) to drive down the residual product and unreacted excess dimethyl sulfate into the filtrate. The solvent was removed on a rotary evaporator. Light orange solid material was transferred into 500 mL cold water and triturated with a spatula in presence of 3.0 mL (equivalent to excess dimethyl sulfate) of ammonium hydroxide solution to neutralize excess dimethyl sulfate. After one hour, the product was collected on a sintered glass funnel, washed with cold water (3×300 mL) and air-dried. Yield was 28.27 g (98.4% of theory). This crude material was 99% pure by HPLC assay which did not require further purification for reductive ring closure. The following analytical results were obtained for this crude product. Its $^1$HNMR in CDCl$_3$ (using tetramethylsilane as an internal reference) showed peaks at δ 7.9 (d, 1H, arom.), 7.75 (d, 1H, atom.), 7.65 (m, 2H, arom.), 7.5 (m, 1H, atom.), 6.55 (2 doublets, 2H, arom.), 4.0 (s, 3H, methoxy), and 3.9 ( s, 3H, methoxy) indicating complete methylation of both phenolic groups of the starting azo dye. Its elemental analysis for the crude sample was determined for $C_{14}H_{13}N_3O_4$ (M.W. 287.3); Calculated: C, 58.53; H, 4.56; N, 14.63. Found: C, 58.36; H, 4.57; N, 14.47.

It should be noted that in the article by J. Rosevear and J. F. K. Wilshire in *Australian Journal of Chemistry*, Vol. 40, Page 1663–1673 (1987), the protected azo dye (XII) is reportedly obtained in 49% yield only whereas the present invention can provide a 98.4% yield.

This crude product, the protected azo dye (XII), was used as such without further purification in the reductive ring closure step as described in the following example.

EXAMPLE 2

(Reductive Ring Closure)

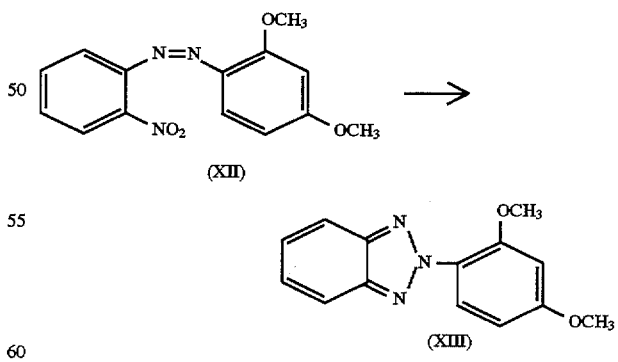

After accomplishing the novel "Direct Protection" step as described in Example 1, the reductive ring closure described in the present Example 2 was routinely done following the procedure described in the J. Rosevear and J. F. K. Wilshire reference making use of thiourea-S,S-dioxide in presence of sodium hydroxide.

Thus, a mixture of the crude protected azo dye (XII) (11.49 g, 0.04 mole), 4N sodium hydroxide (100 mL, 0.4 mole), and methanol (100 mL) was magnetically stirred in an oil bath under argon. When the bath temperature reached 80° C., thiourea-S,S-dioxide (9.52 g, 0.088 mole) was added portion wise. After stirring for 15–20 minutes, the reaction mixture became a suspension of colorless solid in a supernatant dark-brown solution. Then, some more of thiourea-S,S-dioxide (4.76 g, 0.044 mole) was added portion wise. The supernatant liquid rapidly became pale yellow which was stirred for next 30 minutes at the same temperature. It was cooled to room temperature and transferred to an evaporating flask washing down the residual material with acetone (50 mL). Organic solvents from this mixture were removed on a rotary evaporator. The aqueous residue was extracted with methylene chloride (500 mL), dried over anhydrous sodium sulfate which was filtered off and the solvent from the filtrate was removed on the rotary evaporator. The crude thick viscous product of light brown color weighed 10.21 g (100% of theory) which showed one spot on TLC plate. Some more crude product (XIII) from a separate batch of previous step was combined with this batch to be used in the next step. The blue fluorescence of this spot under UV light was a good indicator for protected ring-closed benzotriazole product (XIII). The viscous product solidifies when triturated with a small amount of pentane and kept at room temperature for a few hours. Its $^1$HNMR in $CDCl_3$ using tetramethylsilane as an internal reference showed peaks at δ 7.95 (2 doublets, 2H, arom.), 7.55 (d, 1H, arom.), 7.4 (2 doublets, 2H, arom), 6.6 (m, 2H, atom.), 3.86 (s, 3H, methoxy), and 3.82 (s, 3H, methoxy).

EXAMPLE 3

(Deprotection Step)

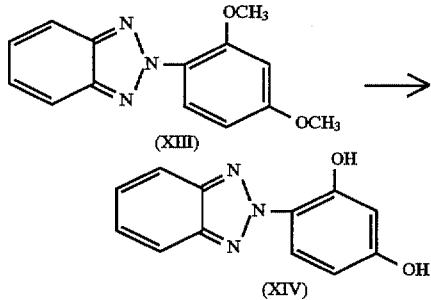

This step could be carried out with crude product (XIII) without its further purification using boron tribromide as a deprotecting reagent following the procedure given in the closest prior art.

The crude material (XIII) (13.99 g, 0.055 mole) was dissolved in methylene chloride (100 mL) and transferred to a 1-L 3-necked round bottom flask equipped with a mechanical stirrer, an ice bath, a water condenser attached with an argon inlet tube through a rubber septum, and a 500-mL capacity pressure equalizing dropping funnel. The reactor was flushed with argon gas and cooled to 0° C. After 10–15 minutes, a 1M solution of boron tribromide in methylene chloride (200 mL, 0.2 mole, 3.6 mole equivalent) was added dropwise to the stirring homogeneous reaction mixture over one hour. After half of its addition, greenish-yellow precipitate appeared. It was stirred for 24 hours while letting it warm up to room temperature. The reaction mixture was poured into 500 mL of ice-water and treated portion wise with solid sodium bicarbonate (67 g, 0.8 mole) while stirring with a glass rod to neutralize hydrobromic acid which was formed in situ. Methylene chloride was removed on a rotary evaporator, the flask was cooled to room temperature and acidified with 1N hydrochloric acid to pH 3–4. The solid product was collected on a sintered glass funnel. It was washed with water (2×200 mL) and air-dried. The HPLC assay of the crude product showed purity over 98%. Yield was 11.71 g (94% of theory). Its FD-MS spectrum showed molecular ion at m/e 227. This product was identical to an authentic sample of (XIV).

The following example, a one-pot process combining all the steps starting from diazotization of 2-nitroaniline, further illustrates its feasibility for manufacturing.

EXAMPLE 4

(A One-pot Process)

This was accomplished on a 0.1 mole scale of 2-nitroaniline as described below in Parts A through D using the same reaction flask. A 4-L 4-necked round bottom flask was chosen in order to handle large volume of reaction mixtures anticipated at any stage during the process.

Part A:

2-Nitroaniline (13.8 g, 0.1 mole) was dissolved in glacial acetic acid (70 mL) by heating on a hot plate. It was cooled to room temperature. Conc. hydrochloric acid (28 mL, 36% solution) was added to form a slurry of 2-nitroaniline hydrochloride. This was done separately in a 500-mL Erlenmeyer flask. It was set for a magnetic stirring in an ice-salt-dry ice bath (−10° C.). Then a solution of sodium nitrite (6.9 g, 0.1 mole) in 20 mL dist. water was added dropwise over 15 min. to the stirring slurry of 2-nitroaniline hydrochloride. A clear light yellow homogeneous solution of the diazonium salt was obtained. This was stirred at the same temperature (−10° to −5° C.) for next 10 min. Resorcinol (12.0 g, about 0.1 mole) was dissolved in 200 mL water in the previously described 4-L reactor which was being cooled in an ice-salt bath and being mechanically stirred, then the diazonium solution was added dropwise through a dropping funnel over 10–15 min. The bright-red azo dye formed instantly. After the complete addition, the reactor was allowed to warm to room temperature as ice melted in the ice-bath. After 2 hours, 1 L water was added to it, stirred, and solid azo dye was allowed to settle (without stirring) for 4 hours. Aqueous part was carefully decanted off from the azo dye. The decanting process was repeated 2 times more in order to remove most of HCl, acetic acid and NaCl. The residual water from the reactor was driven out by azeotropic reflux in 2L of toluene. When no more water came out, toluene was distilled off as much as possible. Residual toluene was removed by using in-house vacuum. Part A is complete at this point while azo dye was not removed from the reactor.

Part B:

The reactor containing the azo dye was charged with dry acetone (600 mL), anhydrous potassium carbonate (69.0 g, 0.5 mole, 5 mole equivalent, although 3 mole equivalent would have been sufficient), and dimethyl sulfate (31.53 g, 0.25 mole, 23.7 mL, density=1.333). The reactor was then heated on a heating mantle to reflux while mechanically stirring for 16–18 hours. It was allowed to cool to room temperature and treated with 3.0 mL of ammonium hydroxide solution. Acetone was distilled off as much as possible. The residual acetone was removed by applying in-house vacuum. This part was accomplished at this point while the methylated (protected) azo dye was not removed from the reactor.

Part C:

The reactor containing the solid material from Part B was charged with 1 L cold water, stirred, allowed to settle down the solid product and the aqueous portion was carefully decanted off. Then the leftover material was diluted with methanol (250 mL) and 4N aqueous NaOH (250 mL). It was mechanically stirred and heated to 80° C. The temperature was controlled with the help of a Therm-O-Watch having a Thermo-couple sensing probe which was inserted into a thermometer pocket. The temperature was held at 80° C. Thiourea-S,S-dioxide (21.6 g, 0.2 mole) was added portion wise over 10–15 min. After stirring for next 15 min. thiourea-S,S-dioxide (11.88 g, 0.11 mole) was added again portion wise over 5 min. The supernatant brown solution rapidly changed to pale yellow. It was stirred at the same temperature for next 30 min. It was cooled to room temperature, diluted with 1 L cold water and left for 16 hours. The cyclized product had settled like gum in the bottom of the reactor. Aqueous layer was decanted off. It was washed and decanted 2 times more with cold water (500 mL each time). The residual water was driven off by azeotropic reflux in cyclohexane. When no more water separated, cyclohexane was distilled off using in-house vacuum. Part C was accomplished at this point without removing the product from the reactor.

Part D:

The heating mantle was replaced with an ice-salt bath. The reactor was charged with dry methylene chloride (200 mL) and mechanically stirred to obtain a homogeneous solution. Then 1M solution of boron tribromide in methylene chloride(400 mL, 0.4 mole, 4 mole equivalent) was added dropwise over 1.5 hours through a dropping funnel under an static pressure of argon gas. Initial homogeneous solution changed to greenish-yellow solid suspension while generating some white fumes which quickly subsided. While stirring, it was allowed to warm to room temperature over 24 hours. Three necks of the reactor were opened. Water was slowly dripped in while cooling in an ice-salt bath. Addition of water continued till no more HBr fumes evolved. It took about 200 mL of water. This was then treated portion wise with solid sodium bicarbonate to neutral pH. At this point, the entire content of the flask was transferred to an evaporating flask. Organic solvent was removed on a rotary evaporator. Aqueous residue was further diluted with 350 mL of water. Insoluble product was collected on a sintered glass funnel, washed with cold water (3×100 mL) and air-dried. Yield was 19.98 g (88% of theory). Its TLC in 1/1 mixture of hexane and ethyl acetate showed one spot corresponding to the desired product.

The following non-limiting examples further illustrate the generality of the process of the present invention.

EXAMPLE 5

(Direct Protection)

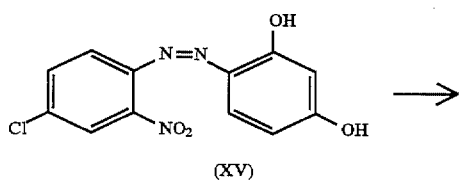

(XV)

→

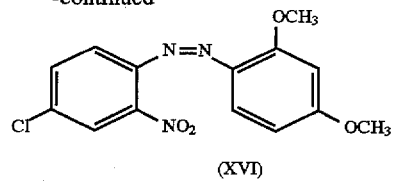

(XVI)

The unprotected azo dye (XV) was prepared in 99% yield by condensing 4-chloro-2-nitrophenyldiazonium chloride (obtained by diazotization of 4-chloro-2-nitroaniline with sodium nitrite in hydrochloric acid) with resorcinol following conventional procedure as known in the art as previously cited. The azo dye (XV) was used in this reaction without further crystallization as it was 98% pure by HPLC assay. A mixture of unprotected azo dye (XV) (110.86 g, 0.38 mole), dimethyl sulfate (142.9 g, 1.133 mole, 107 mL), anhydrous potassium carbonate (168 g, 1.216 mole), and dry acetone (2000 mL) was refluxed in a 2-L 3-necked round bottom flask equipped with a mechanical stirrer, water condenser and argon gas-inlet. The reaction mixture was refluxed for 16 hours with vigorous mechanical stirring. The reaction was monitored by TLC using silica gel coated glass plates and methylene chloride as the developing solvent. The reaction mixture was cooled down to room temperature and filtered through a sintered glass funnel of medium porosity to remove inorganic solid which was well washed with acetone (4×50 mL) to drive down the residual product and unreacted excess dimethyl sulfate into the filtrate. The solvent was removed on a rotary evaporator. Light orange solid material was transferred into 500 mL cold water and triturated with a spatula in presence of 20.0 mL (equivalent to excess dimethyl sulfate) of ammonium hydroxide solution to neutralize excess dimethyl sulfate. After one hour, the product was collected on a sintered glass funnel, washed with cold water (3×300 mL) and air-dried. Yield was 112.24 g (92% of theory). This crude material was 99% pure by HPLC assay showing a retention time 18.3 min. This did not require further purification for reductive ring closure.

It should be noted that the J. Rosevear and J. F. K. Wilshire reference has reported the protected azo dye (XVI) in 63% yield only whereas the present invention provided 92% yield.

This crude product, the protected azo dye (XVI), was used as such without further purification in the reductive ring closure step as described in the following example.

EXAMPLE 6

(Reductive Ring Closure)

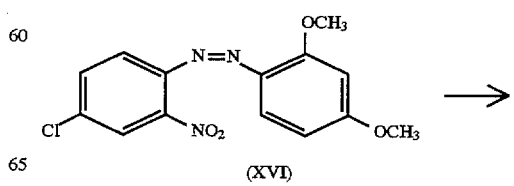

(XVI)

→

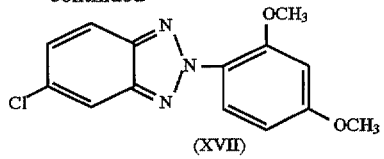

After accomplishing the novel "Direct Protection" step as described in Example 5, the reductive ring closure described in the present Example 6 was routinely done following the procedure given in the closest prior art by making use of thiourea-S,S-dioxide in presence of sodium hydroxide.

Thus, a mixture of the crude protected azo dye (XVI) (96.5 g, 0.3 mole), 4N sodium hydroxide (120 g, 800 mL, 3.0 mole), and methanol (800 mL) was magnetically stirred in an oil bath under argon. When the bath temperature reached 80° C., thiourea-S,S-dioxide (71.36 g, 0.66 mole) was added portion wise. After stirring for 15–20 minutes, the reaction mixture became a suspension of colorless solid in a supernatant dark-brown solution. Then, some more of thiourea-S,S-dioxide (35.68 g, 0.33 mole) was added portion wise. The supernatant liquid rapidly became pale yellow which was stirred for next 30 minutes at the same temperature. It was cooled to room temperature and transferred to an evaporating flask washing down the residual material with acetone (50 mL). Organic solvents from this mixture were removed on a rotary evaporator. The aqueous residue was extracted with methylene chloride (500 mL), dried over anhydrous sodium sulfate which was filtered off and the solvent from the filtrate was removed on the rotary evaporator. The crude thick viscous (later solidified) product of dark brown color weighed 72.21 g (92% of theory) which showed one spot on TLC plate. The blue fluorescence of this spot under UV light was a good indicator for protected ring-closed benzotriazole product (XVII). Its ¹HNMR in CDCl₃ using tetramethylsilane as an internal reference showed peaks at δ 7.9 (m, 2H, arom.), 7.55 (d, 1H, arom.), 7.38 (d, 1H, atom), 6.62 (m, 2H, atom.), 3.9 (s, 3H, methoxy), and 3.85 (s, 3H, methoxy).

EXAMPLE 7

(Deprotection Step)

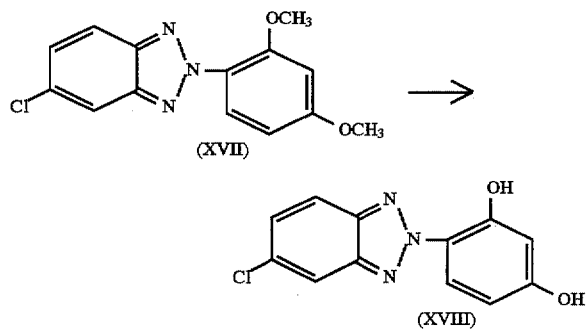

This step could be carried out with crude product (XVII) without its further purification using boron tribromide as a deprotecting reagent following the procedure given in the J. Rosevear and J. F. K. Wilshire reference.

The crude material (XVII) (49.0 g, 0.17 mole) was dissolved in methylene chloride (300 mL) and transferred to a 3-L 3-necked round bottom flask equipped with a mechanical stirrer, an ice bath, a water condenser attached with an argon inlet tube through a rubber septum, and a 500-mL capacity pressure equalizing dropping funnel. The reactor was flushed with argon gas and cooled to 0° C. After 10–15 minutes, an 1M solution of boron tribromide in methylene chloride (600 mL, 0.6 mole, 3.53 mole equivalent) was added dropwise to the stirring homogeneous reaction mixture over one hour. After half of its addition, greenish-yellow precipitate appeared. It was stirred for 24 hours while letting it warm up to room temperature. The reaction mixture was poured into 500 mL of ice-water and treated portion wise with solid sodium bicarbonate to neutral pH while stirring with a glass rod to neutralize hydrobromic acid which was formed in situ. Methylene chloride was removed on a rotary evaporator, the flask was cooled to room temperature. The solid product was collected on a sintered glass funnel. It was washed with water (2×200 mL) and air-dried. The HPLC assay of the crude product showed purity over 98%. Yield was 43.25 g (97% of theory). Its FD-MS spectrum showed molecular ion at m/e 261. Its ¹H NMR in DMSO-d₆ using tetramethylsilane as an internal reference showed peaks at δ 10.25 (broad singlet, 2H, phenolic OH), 8.1 (s, 1H, arom.), 8.0 (s, 1H, arom.), 7.5 (d, 1H, arom), 7.2 (d, 1H, arom), 6.5 (s, 1H, arom.), and 6.4 (d, 1H, arom).

EXAMPLE 8

(Direct Protection)

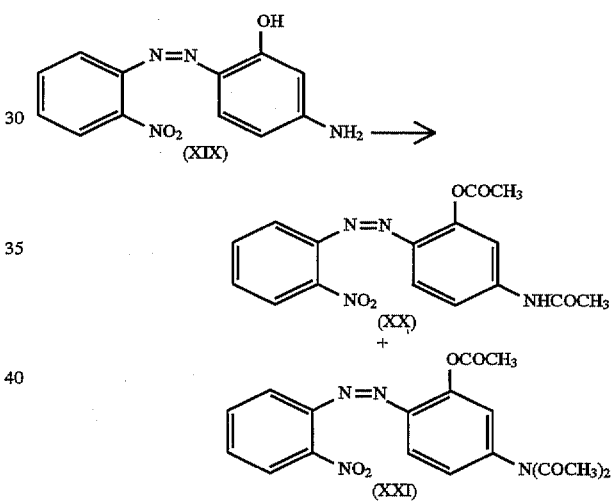

The unprotected azo dye (XIX) was prepared in 98% yield by condensing 2-nitrophenyldiazonium chloride (obtained by diazotization of 2-nitroaniline with sodium nitrite in hydrochloric acid) with 3-aminophenol following conventional procedure as known in the art previously cited. The azo dye (XIX) was used in this reaction without further crystallization as it was over 97% pure by HPLC assay. Thus a mixture of unprotected azo dye (XIX) (10.62 g, 0.041 mole), acetic anhydride (40 g, excess), triethylamine (16.16 g, 0.16 mole, 22.3 mL) and 4-dimethylaminopyridine (DMAP) (0.488 g, 0.004 mole, 10 mole % equivalent) in tetrahydrofuran (250 mL) was magnetically stirred for 3 hours under reflux. The reaction was monitored by TLC (CH₂Cl₂) for disappearance of starting azo dye (XIX). The solvent was removed on a rotary evaporator, the residue was diluted with acetone (50 mL) and poured into cold water (500 mL) while stirring with a glass rod), precipitate was filtered, washed with cold water (2×200 mL), and air-dried. This crude material was a mixture of diacylated azo dye (XX) and triacylated azo dye (XXI) which weighed 12.93 g. These were in an approximately 1:1 ratio according to an HPLC assay and Mass Spectral analysis. Optionally, this reaction could be carried out in acetic anhydride, glacial acetic acid and anhydrous sodium acetate under reflux condition.

EXAMPLE 9

(Reductive Ring Closure)

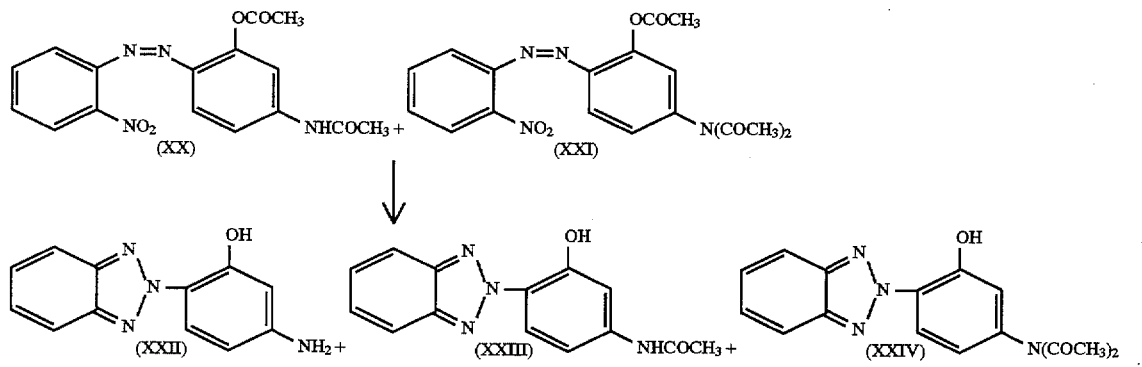

This reaction was carried out following the general procedure as mentioned in Example 2 using thiourea-S,S-dioxide as the reducing agent. The mixture of protected azo dyes (XX) and (XXI) (13.69 g) and thiourea-S,S-dioxide (14.26 g, 0.132 mole) were used. The usual work-up of the reaction afforded 7.83 g of the crude material, which showed a mixture of (XXII) (~6%), monoacetylated ring closed product (XXIII) (~47%), and diacetylated ring closed product (XXIV) (~47%) as identified by HPLC assay, and their respective UV absorption curve shape in HPLC and mass spectral analysis. The inventor recognizes an added advantage in this reaction that final desired product (XXII) may be easily obtained from the same pot reaction by in situ basic hydrolysis of (XXIII) and (XXIV) at 130° C. for 3–4 hours without isolating and further converting either one of these two to (XXII) in over 90% yield. Optionally, the crude mixture of ring-closed products was isolated, and then was subjected to acidic or basic hydrolysis to obtain the desired product (XXII).

The following example further illustrates this added advantage of in situ hydrolysis (methanolysis in this case) leading to the desired end product.

EXAMPLE 10

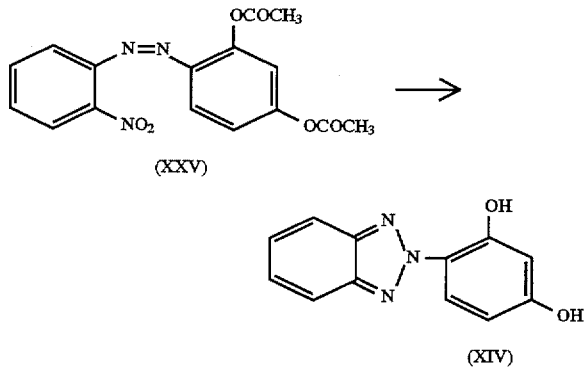

The protected azo dye (XXV) was synthesized in quantitative yield by diacylating the corresponding unprotected azo dye with acetic anhydride in methylene chloride or in tetrahydrofuran in presence of triethylamine as a base and 4-dimethylaminopyridine as a catalyst. Thus, when a mixture of the protected azo dye (XXV) (0.343 g, 0.001 mole), anhydrous ammonium formate (0.63 g, 0.01 mole), and 10% Pd-C was stirred in dry methanol at room temperature for 6–10 hours followed by 6–10 hours reflux, formation of ring closed unprotected desired product (XIV) was indicated by HPLC-generated UV absorption curve and mass spectral analysis showing molecular ion at m/e 227.

EXAMPLE 11

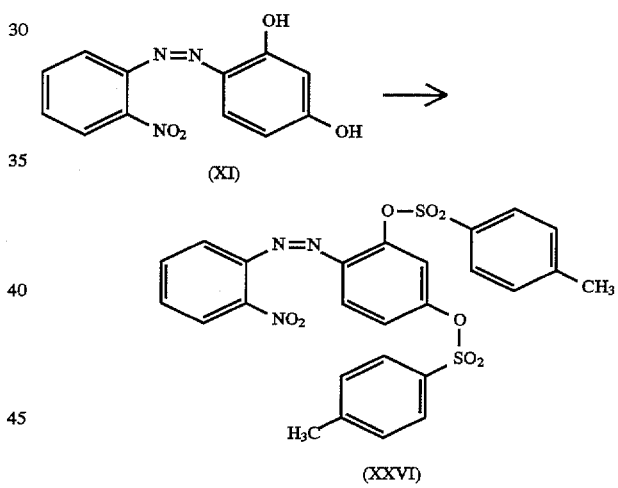

This example illustrates the use of p-toluenesulfonyl group as the protecting group. Thus, the azo dye (XI) (12.6 g, 0.048 mole) and p-toluenesulfonyl chloride (20.38 g, 0.107 mole) were placed in a 3-necked 2-L capacity round-bottom flask equipped with a mechanical stirrer and an ice-bath. Acetone (1,000 mL) was added and stirred at 0° C. Triethylamine (12.3 g, 0.122 mole, 17 mL) was added over 1–2 min followed by 4-N,N-dimethylaminopyridine (0.31 g, 0.0025 mole) in one portion. After 30 min. the ice-bath was removed and allowed to attain the room temperature. The reaction was completed within 2 hours as monitored by TLC (CH$_2$Cl$_2$/MeOH; 99.8/0.2) showing one spot with an Rf=0.58. The solvent was removed on a rotary evaporator. The residue was diluted with one liter cold water. The product gummed out as red-brown thick oil. The turbid supernatant liquid was decanted off. The residue was extracted with methylene chloride (500 mL), washed with brine (500 mL), dried over anhydrous sodium sulfate. This was filtered and the solvent was removed on a rotary evaporator. The yield of the desired di-protected azo dye (XXVI) was 27.56 g (99.9% of theory). Its FD Mass Spectrum showed the molecular ion peak at m/e 567. Its HPLC showed a peak with retention time 20.4 min. The HPLC-generated curve had a $\delta_{max}$ 333 nm. Its $^1$H NMR (CDCl$_3$) showed peaks at δ 7.9 (t, 2H, arom), 7.7 (d, 2H, arom), 7.6 (2 doublets merged with each other, 4H, atom), 7.44 (d, 1H, atom), 7.38 (d, 2H, atom), 7.15 (d, 1H, arom), 7.0 (s, 1H, atom), 6.95 (d, 1H, arom), 2.5 (s, 3H, CH$_3$) and 2.3 (s, 3H, CH$_3$).

EXAMPLE 12

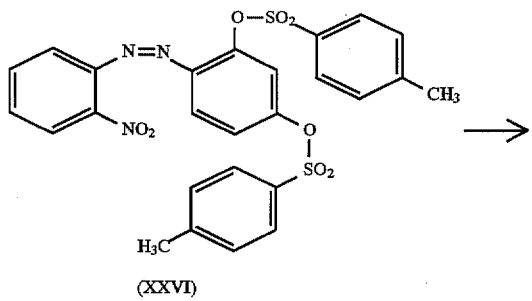

(XXVI)

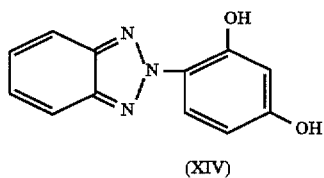

(XIV)

This example illustrates that the reductive ring closure and deprotection can be carried out in one-pot. This reaction was performed the same way as in Example 6. The azo dye (XXVI) (27.0 g, 0.0476 mole) was reacted with thiourea-S, S-dioxide (17.07 g, 0.157 mole) in the presence of methanol (238 mL) and sodium hydroxide (38.08 g, 0.95 mole) solution in water (238 mL) at 80° C. for about 3 hours under argon. The HPLC assay of its aliquot (which was acidified with hydrochloric acid) indicated a mixture of desired product (XIV) (~70%, Retention time 13.3 min) and its 4'-substituted monosulfonate (~26%, Retention time 19.15 min) contaminated with a trace amount of its N-oxide. The temperature was raised to 130° C. and refluxed for 16 hours for complete in situ hydrolysis of the sulfonate ester group. Methanol was distilled off. The aqueous residue was cooled to 0° C., diluted with 1,000 mL cold water and acidified with conc. hydrochloric acid to pH 3–4. The entire content was transferred to a separatory funnel and extracted with ethyl acetate (3×500 mL). The extract was dried over anhydrous sulfate and filtered. The solvent was removed on a rotary evaporator. The product (XIV) was obtained as a light-brown solid which weighed 10.26 g (95% of theory).

EXAMPLE 13

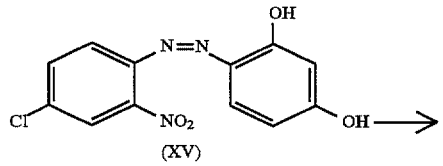

(XV)

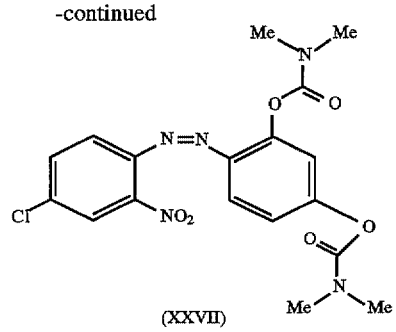

(XXVII)

This example illustrates that dimethylcarbamyl group is an effective protecting group. Thus, the azo dye (XV) (58.74 g 0.2 mole) and acetone (1,500 mL) were placed in a 3-necked 2-L capacity round-bottom flask equipped with a mechanical stirrer and an ice-bath. While stirring at 0° C., dimethyl carbamyl chloride (47.32 g, 0.45 mole, 40.5 mL) was added over 2–3 min. Triethylamine (45.5 g, 0.45 mole, 63 mL) was added slowly through a dropping funnel to the stirring reaction mixture over 10–15 min. Copious white fumes which appeared in the beginning of this addition, subsided after about 10 min. N,N-Dimethylaminopyridine (2.45 g 0.02 mole) was added in one portion. The ice-bath was removed after about 15 min and the reaction mixture was allowed to attain the room temperature. It was refluxed on a heating mantle for 2.5 hours. The reaction was complete as indicated by TLC (CH$_2$Cl$_2$/MeOH; 9.5/0.5) showing one spot with Rf 0.9 for di-protected azo dye (XXVII). The solvent was removed on a rotary evaporator. The residue was triturated with 1,000 mL cold water. Insoluble product was filtered on a sintered glass funnel, washed with cold water (3×200 mL). The mud-color looking solid was air-dried which weighed 83.21 g (95.4% of theory). The crude material was analytically pure. Its FD Mass spectrum shoed the molecular ion peak at m/e 435. Its HPLC showed a peak with retention time 16.8 min and with peak area percent 98.7%. The HPLC-generated absorption curve shoed $\delta_{max}$ at 358 nm and a hump at 445 nm. Its $^1$HNMR (CDCL$_3$) showed peaks at δ 7.9 (s, 1H, atom), 7.6 (d, 1H, arom), 7.5 (d, 1H, arom), 7.2 (s, 1H, arom), 7.1 (d, 1H, arom), 6.78 (d, 1H, arom), 3.15 (s, 3H, NCH$_3$), 3.08 (s, 3H, NCH$_3$) and 3.02 (s, 6H, N(CH$_3$)$_2$). Elemental analysis calcd for C$_{18}$H$_{18}$Cl$_1$N$_5$O$_6$: C, 49.61; H, 4.16; N, 16.07; Cl, 8.13. Found: C, 49.77; H, 4.31; N, 15.89; Cl, 8.03.

EXAMPLE 14

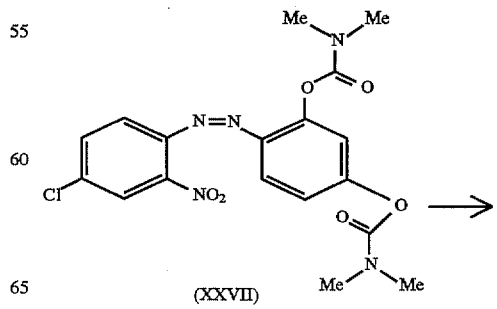

(XXVII)

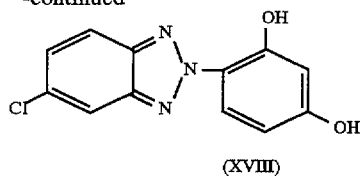

(XVIII)

This example illustrates that the reductive ring closure and deprotection can be carried out in one-pot. This reaction was performed the same way as in Example 6 in a 2-L capacity 3-necked round-bottom flask equipped with a mechanical stirrer and an oil-bath and argon gas inlet attached through a reflux condenser. The azo dye (XXVII) (52.3 g, 0.12 mole) was reacted with thiourea-S,S-dioxide (42.84 g, 0.396 mole) in the presence of methanol (300 mL) and sodium hydroxide (48.0 g, 1.2 mole) solution in water (300 mL) at 80° C. for about 3 hours. The HPLC assay of its aliquot (which was acidified with hydrochloric acid) indicated a mixture of desired product (XVIII) (~75%, retention time 14.86 min) and its 4'-substituted monocarbamate (~25%, retention time 13.85 min). More sodium hydroxide (40 g, 0.1 mole) was added and the temperature was raised to 130° C. and refluxed for 16 hours for complete in situ hydrolysis of the carbamate group. Methanol was distilled off. The aqueous residue was cooled to 0° C., diluted with 1,000 mL cold water and acidified with conc. hydrochloric acid to pH 3–4. The entire content was transferred to a separatory funnel and extracted with ethyl acetate (3×500 mL). The extract was dried over anhydrous sulfate and filtered. The solvent was removed on a rotary evaporator. The product (XVIII) was obtained as a brown solid which weighed 29.75 g (95% of theory).

The same transformation was accomplished with sodium dithionite ($Na_2S_2O_4$) as the reducing agent shown in the following example.

EXAMPLE 15

This reaction was performed the same way as in Example 6 in a 250-mL capacity 3-necked round-bottom flask equipped with a mechanical stirrer and an oil-bath and argon gas inlet attached through a reflux condenser. The azo dye (XXVII) (8.7 g, 0.02 mole) was reacted with sodium dithionite (17.4 g, 0.1 mole) by adding this crystalline powder in small portions in the presence of methanol (50 mL) and sodium hydroxide (16.0 g, 0.4 mole) solution in water (50 mL) at 80° C. over 10–15 min. After complete addition of sodium dithionite, the color of the reaction mixture changed from light brown to dark brown. After 15 min, the temperature was raised to 120° C. when the reaction mixture started refluxing. The color of the reaction mixture then changed in sequence from dark brown to dark red to orange to dark yellow to muddy yellow. The final color stayed there as long as the reaction mixture was not exposed to air. After 2 hours of reflux it was cooled to room temperature. When it was opened to air, the color changed to dark green. Methanol was removed on a rotary evaporator. The dark green aqueous residue was diluted with cold water (500 mL). It was acidified with conc. hydrochloric acid to pH 3–4. The gelatinous precipitate was extracted with ethyl acetate (500 mL+200 mL). The combined extract was dried over anhydrous sodium sulfate which was filtered off, and then the solvent was removed on a rotary evaporator. A brown viscous material was obtained which solidified on keeping at room temperature. It weighed 5.1 g (97.5% of theory). The HPLC analysis of the crude material showed a peak with retention time 14.79 min and 95% purity by peak area percent.

The following comparative examples illustrate that when the reductive ring closure was attempted with unprotected azo dyes the ring-closed product was obtained either in lower yield or unwanted side-product(s) resulted.

EXAMPLE 16

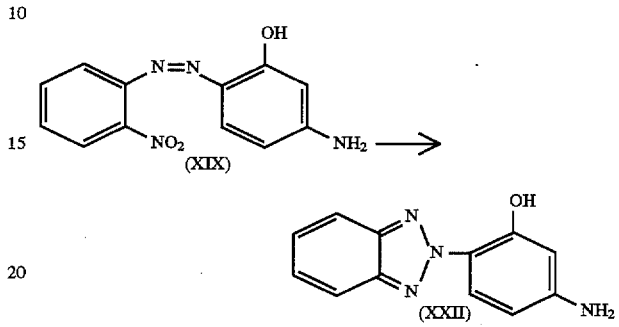

This reaction was done under identical conditions as described in Example 9 using the following amounts of reactants/reagents: the unprotected azo dye (XIX) (20.60 g, 0.08 mole), Thiourea-S,S-dioxide (28.53 g, 0.264 mole), 4N NaOH (150 mL, 0.48 mole), and MeOH (150 mL). The usual work up of the reaction mixture gave 4.25 g (24% of theory) crude yield of desired product (XXII). Whereas in Invention Example 9 its yield was over 90%. In one of the closest prior arts, [See, H. S. Freeman and J. C. Posey, Jr., Dyes and Pigments, Vol. 20, page 171–195 (1992)], only 59% yield of 5-chloro substituted analog of (XXII) has been reported. The present inventor anticipated high yield if the amino group or the both phenolic and amino groups the corresponding azo dye were protected. Although this trend was quite clear in the said prior art (see page 176), the effect of protection on the ring closure chemistry is not mentioned.

EXAMPLE 17

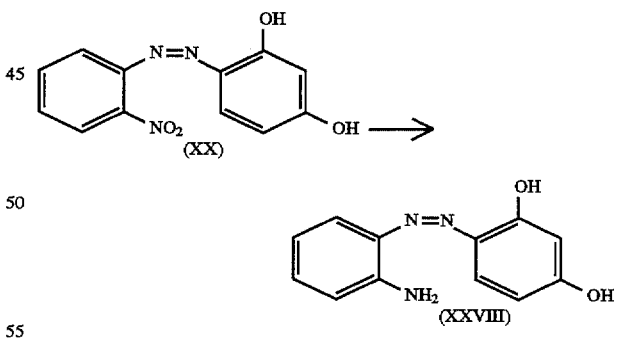

This reaction was carried out under identical conditions as described in Example 2 using the following amounts of reactants/reagents: unprotected azo dye (XI) (20.73 g, 0.08 mole), thiourea-S,S-dioxide (28.53 g, 0.264 mole), 4N NaOH (200 mL, 0.48 mole), and MeOH (150 mL). During this reaction, the starting unprotected azo dye (XI) was completely consumed within 15 minutes. In TLC (of acidified aliquot) did not indicate any amount of desired ring-closed product (XIV), instead showed a spot corresponding to a highly polar material such as (XXVIII) which was confirmed by HPLC-generated UV-VIS absorption curve corresponding to that of the amino substituted azo dye (XXVIII), and by its mass spectral analysis showing its molecular ion at m/e 229. This confirms that if azo dye is unprotected, the nitro group gets reduced to amino group and no ring closure takes place.

The preceding examples are set forth to illustrate specific embodiments of this invention and are not intended to limit the scope of the compositions or materials of the invention. It will be understood that variations and modifications can be effected within the spirit and scope of the invention.

I claim:

1. A method for preparing a compound of formula (VII):

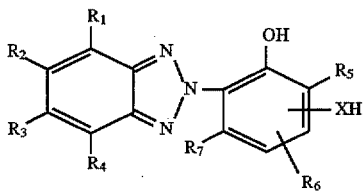

wherein:

$R_1$, $R_2$, $R_3$, $R_4$, $R_5$, $R_6$ and $R_7$ are, indepedently: H; halogen; cyano; —$CO_2Y$ where Y is H or a 1 to 12 carbon alkyl or a 6 to 12 carbon aryl group; 1 to 12 carbon atom carbamoyl group; 0 to 12 carbon atom sulfoxido group; 0 to 12 carbon atom sulfonyl group; 0 to 12 carbon atom sulfonato group; 0 to 12 carbon atom sulfonamido group; 1 to 18 carbon atom alkyl group; 1 to 18 carbon atom alkoxy group; 6 to 20 carbon atom aryl group; 5 to 20 atom heteroaryl group having 1 to 4 heteroatoms selected from O, N or S; 6 to 20 carbon atom aryloxy group; or any two or more of adjacent ones of $R_1$ through $R_4$, or $R_6$ and $R_7$ together, or $R_6$ and $R_5$ together when they are adjacent one another, may together form a 1 to 10 cabon atom alicyclic group, or complete, together with the carbon atoms of the benzene ring to which they are attached, a 6 to 20 carbon atom aromatic group or a 5 to 20 atom heteroaryl group having 1 to 4 heteroatoms selected from O, N or S; or $R_7$ is OH;

X is O, S, or $NR_8$ where $R_8$ is H, 1 to 12 carbon alkyl or aryl group, or 5 to 20 atom heteroaryl group having 1 to 4 heteroatoms selected from O, N or S;

the method comprising:

protecting at least —XH on a compound of formula (IV) below to form a protected formula (IV) compound, by forming —X(PG) where PG is a group other than H which is not removed during a subsequent ring closure step:

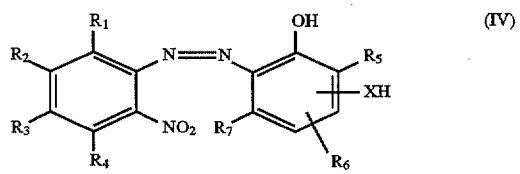

wherein $R_1$ to $R_7$ and X are as defined above for formula (VII);

performing a ring closure by reacting the protected formula (IV) compound with a reducing agent to form a compound of formula (VI):

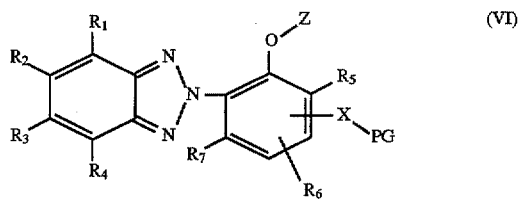

wherein Z is H or a protecting group;

deprotecting the compound of formula (VI) to form the compound of formula (VII) by replacing PG with H and, when Z is not H, also replacing Z with H.

2. A method according to claim 1 wherein —OH is also protected on formula (IV) prior to the ring closure step, to form —$O(PG_1)$, wherein $PG_1$ is a group other than H which is not removed during a subsequent ring closure step or is a 1–12 carbon atom acyl group, 1 to 24 carbon atom carbamyl group, or a 1 to 12 carbon atom sulfonyl group.

3. A method according to claim 2 wherein the acyl group which $PG_1$ may represent is a 2–12 carbon atom acyl group.

4. A method according to claim 1 wherein PG is selected from: 1–18 carbon atom alkyl groups with or without 1 to 6 intervening oxygen, sulfur or nitrogen atoms; 1–18 carbon atom acyl group; 1 to 24 carbon atom carbamyl group; 1 to 18 carbon atom sulfonyl group; benzyl group; tetrahydropyranyl group; and 3 to 20 carbon atom trialkyl silyl group.

5. A method according to claim 2 wherein PG and $PG_1$ are, independently, selected from: 1–18 carbon atom alkyl group with or without 1 to 6 intervening oxygen, sulfur or nitrogen atoms; 1–18 carbon atom acyl group; 1 to 24 carbon atom carbamyl group; 1 to 18 carbon atom sulfonyl group; benzyl group; tetrahydropyranyl group; and 3 to 20 carbon atom trialkyl silyl group.

6. A method according to claim 1 wherein PG is selected from: methyl; ethyl; n-propyl; isopropyl; butyl; pentyl; t-butyl; t-amyl; methoxymethyl; methoxyethoxymethyl; formyl; acetyl; benzoyl; $SO2R_{10}$ where $R_{10}$ is selected from methyl, ethyl, phenyl or p-toluenesulfonyl; 1 to 12 carbon atom dialkyl carbamyl; benzyl group; tetrahydropyranyl group; and 3 to 20 carbon atom trialkyl silyl group; or $COR_9$ where $R_9$ is methyl, ethyl or phenyl; phenyl group; pyridinyl; imidazoyl; pyrrolyl; furyl; and thienyl.

7. A method according to claim 2 wherein PG and $PG_1$ are, independently, selected from: methyl; ethyl; n-propyl; isopropyl; butyl; pentyl; t-butyl; t-amyl; methoxymethyl methoxyethoxymethyl; formyl; acetyl; benzoyl; $SO2R_{10}$ where $R_{10}$ is selected from methyl, ethyl, phenyl or p-toluenesulfonyl; 1 to 12 carbon atom dialkyl carbamyl; benzyl group; tetrahydropyranyl group; and 3 to 20 carbon atom trialkyl silyl group; or $COR_9$ where $R_9$ is methyl, ethyl or phenyl; phenyl group; pyridinyl; imidazoyl; pyrrolyl; furyl; and thienyl.

8. A method according to claim 1 wherein, when $R_7$ is OH that OH is also protected on formula (IV) prior to the ring closure step, to form —$O(PG_1)$, wherein $PG_1$ is a group other than H which is not removed during a subsequent ring closure step or is a 1–12 carbon atom acyl group, 1 to 24 carbon atom carbamyl group, or a 1 to 12 carbon atom sulfonyl group.

9. A method according to claim 2 wherein, when $R_7$ is OH that OH is also protected on formula (IV) prior to the ring closure step, to form —$O(PG_1)$, wherein $PG_1$ is a group other than H which is not removed during a subsequent ring closure step or is a 1–12 carbon atom acyl group, 1 to 24 carbon atom carbamyl group, or a 1 to 12 carbon atom sulfonyl group.

10. A method according to claim 9 wherein each $PG_1$ and PG are, independently, selected from: methyl; ethyl;

n-propyl; isopropyl; butyl; pentyl; t-butyl; t-amyl; methoxymethyl; methoxyethoxymethyl; formyl; acetyl; benzoyl; $SO_2R_{10}$ where $R_{10}$ is selected from methyl, ethyl, phenyl or p-toluenesulfonyl; 1 to 12 carbon atom dialkyl carbamyl; benzyl group; tetrahydropyranyl group; and 3 to 20 caron atom trialkyl silyl group; or $COR_9$ where $R_9$ is methyl, ethyl or phenyl; phenyl group; pyridinyl; imidazoyl; pyrrolyl; furyl; and thienyl.

11. A method according to claim 9 wherein $R_7$ is H or OH.

12. A method for preparing a compound of formula (VII):

(VII)

wherein:

$R_1$, $R_2$, $R_3$, $R_4$, $R_5$, $R_6$ and $R_7$ are, indepedently: H; halogen; cyano; —$CO_2Y$ where Y is H or a 1 to 12 carbon alkyl or a 6 to 20 carbon atom aryl group; 1 to 12 carbon atom carbamoyl group; 0 to 12 carbon atom sulfoxido group; 0 to 12 carbon atom sulfonyl group; 0 to 12 carbon atom sulfonato group; 0 to 12 carbon atom sulfonamido group; 1 to 18 carbon atom alkyl group; 1 to 18 carbon atom alkoxy group; 6 to 20 carbon atom aryl group; 5 to 20 atom heteroaryl group having 1 to 4 heteroatoms selected from O, N or S; 6 to 20 carbon atom aryloxy group; or any two or more of adjacent ones of $R_1$ through $R_4$, or $R_6$ and $R_7$ together, or $R_6$ and $R_5$ together when they are adjacent one another, may together form a 1 to 10 cabon atom alicyclic group, or complete, together with the carbon atoms of the benzene ring to which they are attached, a 6 to 20 carbon atom aromatic group or a 5 to 20 atom heteroaryl group having 1 to 4 heteroatoms selected from O, N or S; or $R_7$ is OH;

X is O, S, or $NR_8$ where $R_8$ is H, 1 to 12 carbon alkyl or aryl group, or 5 to 20 atom heteroaryl group having 1 to 4 heteroatoms selected from O, N or S;

the method comprising:

diazotizing the compound of formula (I) with an aqueous acidic nitrite salt to obtain the compound of formula (II) and coupling the compound of formula (II) with the compound of formula (III) to obtain the compound of formula (IV) as shown below:

(IV)

wherein $R_1$ to $R_7$ and X are as defined above for formula (VII);

protecting at least —XH on a compound of formula (IV) below to form a protected formula (IV) compound, by forming —X(PG) where PG is a group other than H which is not removed during a subsequent ring closure step;

performing a ring closure by reacting the protected formula (IV) compound with a reducing agent to form a compound of formula (VI):

(VI)

wherein Z is H or a protecting group;

deprotecting the compound of formula (VI) to form the compound of formula (VII) by replacing PG with H and, when Z is not H, also replacing Z with H.

13. A method according to claim 1 wherein the ring closure step comprises reacting the protected formula (IV) compound with a reducing agent selected from a thiourea-S,S-dioxide and a dithionite salt in a basic aqueous solution.

14. A method according to claim 13 wherein the aqueous solution is an alcoholic solution.

15. A method according to claim 14 wherein the temperature is maintained at 60° to 80° C.

16. A method according to claim 15 wherein the ring closure step is performed for 2 to 3 hours.

17. A method according to claim 1 wherein the ring closure step comprises the catalytic hydrogenation of the protected formula (IV) compound.

18. A method according to claim 1 wherein the ring closure step comprises reacting with a formate salt in the presence of a catalyst.

19. A method according to claim 18 wherein the catalyst is a palladium-charcoal catalyst.

20. A method according to claim 1 wherein PG is selected from a 1 to 18 carbon atom alkyl group or a benzyl group, and the compound of formula (VI) is deprotected in the presence of a boron trihalide in a halogenated hydrocarbon solvent.

21. A method according to claim 1 wherein PG is selected from 1–18 carbon atom acyl group, 1 to 24 carbon atom carbamyl group, or 1 to 18 carbon atom sulfonyl group, and the compound of formula (VI) is deprotected by aqueous acidic or basic hydrolysis.

22. A method according to claim 1 wherein PG is selected from a benzyl group or a tetrahydropyranyl group, and the compound of formula (VI) is deprotected by reacting with an aqueous mineral acid.

23. A method according to claim 22 wherein the mineral acid is hydrochloric acid.

24. A method according to claim 1 wherein PG is selected from a 3 to 20 carbon atom trialkyl silyl group, and the compound of formula (VI) is deprotected by reacting with an aqueous fluoride salt in the presence of an organic co-solvent.

25. A method according to claim 1 wherein: $R_3$ is F, Cl, Br, cyano, 1 to 18 carbon atom alkoxy group, or 0 to 12 carbon atom sulfonyl group; $R_7$ is H or OH; $R_5$ and $R_6$ are independently a 1 to 12 carbon atom alkyl or H; and $R_1$ and $R_2$ are independently H, Cl or a 1 to 18 carbon atom alkoxy group.

26. A method according to claim 1 wherein all of the described reaction steps are performed without isolating products other than the compound of formula (VII).

27. A method according to claim 2 wherein all of the described reaction steps are performed without isolating products other than the compound of formula (VII).

28. A method according to claim 12 wherein all of the described reaction steps are performed without isolating products other than the compound of formula (VII).

* * * * *